(12) United States Patent
Burk

(10) Patent No.: US 8,455,547 B2
(45) Date of Patent: Jun. 4, 2013

(54) SUBSTITUTED CYCLOPENTANES HAVING PROSTAGLANDIN ACTIVITY

(75) Inventor: Robert M. Burk, Laguna Beach, CA (US)

(73) Assignee: Allergan, Inc., Irvine, CA (US)

( * ) Notice: Subject to any disclaimer, the term of this patent is extended or adjusted under 35 U.S.C. 154(b) by 243 days.

(21) Appl. No.: 12/363,996

(22) Filed: Feb. 2, 2009

(65) Prior Publication Data

US 2009/0197962 A1 Aug. 6, 2009

Related U.S. Application Data

(60) Provisional application No. 61/026,179, filed on Feb. 5, 2008.

(51) Int. Cl.
*A61K 31/5575* (2006.01)
*C07C 405/00* (2006.01)

(52) U.S. Cl.
USPC .......................................... 514/573; 562/503

(58) Field of Classification Search
USPC .......................................... 514/573; 562/503
See application file for complete search history.

(56) References Cited

U.S. PATENT DOCUMENTS

| 7,091,231 B2 | 8/2006 | Donde |
| 2005/0070516 A1 | 3/2005 | Wilson |

FOREIGN PATENT DOCUMENTS

| DE | 2228154 A * | 2/1975 |
| EP | 0 116 358 | 8/1984 |
| EP | 1759702 A1 | 3/2007 |
| WO | WO 98/33497 | 8/1998 |
| WO | WO 01/74313 A2 | 10/2001 |
| WO | WO 2005/013928 A1 | 2/2005 |
| WO | WO 2006/063179 | 6/2006 |
| WO | WO 2007/060453 | 5/2007 |
| WO | WO 2007/149312 A2 | 12/2007 |

OTHER PUBLICATIONS

Spilman et al. Prostaglandins, 1977, 13, 795-805.*
CAPLUS record of DE 2228154, 1973.*
Giron, D. J. Therm. Anal. Cal. 2001, 64, pp. 37-60.*
Giron, D. J. Therm. Anal. Cal. 2002, 68, pp. 335-357.*
B. Rodriquez-Spong et al. Advanced Drug Delivery Reviews, 2004, 56, pp. 241-274.*
Souillac, et al., Characterization of Delivery Systems, Differential Scanning Calorimetry, pp. 217-218 (in Encyclopedia of Controlled Drug Delivery, 1999, John Wiley & Sons pp. 212-227).*
Rautio et al. Nature Reviews Drug Discovery 2008, 7, pp. 255-270.*
Wang et al. Drug Delivery: Principles and Applications, 2005 John Wiley & Sons, Inc. Publication, Section 8.3, pp. 136-137.*
Smith, D. A. Current Opinion in Drug Discovery & Development 2007, 10, 550-559.*
Testa, B. Current Opinion in Chemical Biology 2009, 13, pp. 338-344.*
CAplus entry for Steffenrud, S. Biochemical Medicine, 1984, 32, 161-180.*
American Health Assistance Foundation, Glaucoma Risk Factors and Prevention (http://www.ahaf.org/glaucoma/about/risk.html), accessed Sep. 5, 2012.*
Emedicinehealth, Ocular Hypertension (http://www.emedicinehealth.com/ocular_hypertension/page12_em.htm), accessed Sep. 5, 2012.*
Richard B. Silverman, "Prodrugs and Drug Delivery System", Organic Chemistry of Drug Design and Drug Interaction, 2d Ed., Elsevier Academic Press: Amsterdam, 2004, pp. 497-557.

* cited by examiner

*Primary Examiner* — Rebecca Anderson
*Assistant Examiner* — Matthew Coughlin
(74) *Attorney, Agent, or Firm* — Lorenz Siddiqi; Kevin J. Forrestal

(57) ABSTRACT

Therapeutic compounds, compositions, methods, and medicaments related thereto are disclosed herein.

12 Claims, No Drawings

SUBSTITUTED CYCLOPENTANES HAVING PROSTAGLANDIN ACTIVITY

RELATED APPLICATION DATA

This application claims the benefit of U.S. Provisional Application Ser. No. 61/026,179 filed Feb. 5, 2008, which is hereby incorporated by reference in its entirety.

DESCRIPTION OF THE INVENTION

Ocular hypotensive agents are useful in the treatment of a number of various ocular hypertensive conditions, such as post-surgical and post-laser trabeculectomy ocular hypertensive episodes, glaucoma, and as presurgical adjuncts.

Glaucoma is a disease of the eye characterized by increased intraocular pressure. On the basis of its etiology, glaucoma has been classified as primary or secondary. For example, primary glaucoma in adults (congenital glaucoma) may be either open-angle or acute or chronic angle-closure. Secondary glaucoma results from pre-existing ocular diseases such as uveitis, intraocular tumor or an enlarged cataract. Glaucoma occurs in about 2% of all persons over the age of 40 and may be asymptotic for years before progressing to rapid loss of vision.

The underlying causes of primary glaucoma are not yet known. The increased intraocular tension is due to the obstruction of aqueous humor outflow. In chronic open-angle glaucoma, the anterior chamber and its anatomic structures appear normal, but drainage of the aqueous humor is impeded. In acute or chronic angle-closure glaucoma, the anterior chamber is shallow, the filtration angle is narrowed, and the iris may obstruct the trabecular meshwork at the entrance of the canal of Schlemm. Dilation of the pupil may push the root of the iris forward against the angle, and may produce pupilary block and thus precipitate an acute attack. Eyes with narrow anterior chamber angles are predisposed to acute angle-closure glaucoma attacks of various degrees of severity.

Secondary glaucoma is caused by any interference with the flow of aqueous humor from the posterior chamber into the anterior chamber and subsequently, into the canal of Schlemm. Inflammatory disease of the anterior segment may prevent aqueous escape by causing complete posterior synechia in iris bombe, and may plug the drainage channel with exudates. Other common causes are intraocular tumors, enlarged cataracts, central retinal vein occlusion, trauma to the eye, operative procedures and intraocular hemorrhage.

In cases where surgery is not indicated, prostaglandins and prostamides have recently become the first line treatments of glaucoma. Certain eicosanoids and their derivatives are currently commercially available for use in glaucoma management. Eicosanoids and derivatives include numerous biologically important compounds such as prostaglandins and their derivatives. Prostaglandins can be described as derivatives of prostanoic acid which have the following structural formula:

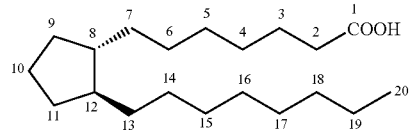

Various types of prostaglandins are known, depending on the structure and substituents carried on the alicyclic ring of the prostanoic acid skeleton. Further classification is based on the number of unsaturated bonds in the side chain indicated by numerical subscripts after the generic type of prostaglandin [e.g. prostaglandin $E_1$ ($PGE_1$), prostaglandin $E_2$ ($PGE_2$)], and on the configuration of the substituents on the alicyclic ring indicated by $\alpha$ or $\beta$ [e.g. prostaglandin $F_{2\alpha}$ ($PGF_{2\beta}$)].

Disclosed herein are compounds represented by the formula:

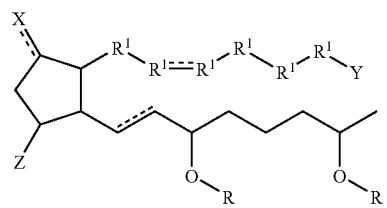

wherein a dashed line represents the presence or absence of a bond;

Y has from 0 to 14 carbon atoms and is: an organic acid functional group, or an amide or ester thereof; hydroxymethyl or an ether thereof; or a tetrazolyl functional group;

X is halo, =O, =S, —SH, —CF$_3$, —CN, =CH$_2$, =CHalkyl or =C(alkyl)$_2$ having from 1 to 6 carbon atoms;

Z is halo, —OH, —OR, —SH, —CF$_3$, or —CN;

each $R^1$ is independently O, S, CH$_2$, or if $R^1$ forms a double bond to another $R^1$, then both are CH, provided that O-O, S-O, and O—S are not present, and each R is independently —H, $C_{1-6}$ alkyl, $C_{1-6}$ hydroxyalkyl, or $C_{1-6}$ acyl.

These compounds are useful for reducing intraocular pressure. Reduction of intraocular pressure has been shown to delay or prevent the onset of primary open angle glaucoma, and to delay or prevent further vision loss in patients with primary open angle glaucoma. Thus, these compounds are also useful for treating glaucoma. These compounds are also useful for growing hair, including one or more of: increasing the number of individual hairs, increasing the length of individual hairs, and increasing the width or thickness of individual hairs. These compounds are also useful for improving the appearance of hair, including increasing its gloss, shine, or other properties related to the reflection or dispersion of light, as well as changing the color of hair, including changing hair from grey or white to the color the hair was before it turned grey or white, such as red, brown, or black.

Different types of suitable dosage forms and medicaments are well known in the art, and can be readily adapted for delivery of the compounds disclosed herein. For example, the compound could be dissolved or suspended in an aqueous solution or emulsion that is buffered to an appropriate pH, and administered topically to an eye of a mammal (see U.S. Pat. No. 7,091,231).

For the purposes of this disclosure, "treat," "treating," or "treatment" refer to the use of a compound, composition, therapeutically active agent, or drug in the diagnosis, cure, mitigation, treatment, or prevention of disease or other undesirable condition.

Unless otherwise indicated, reference to a compound should be construed broadly to include compounds, pharmaceutically acceptable salts, prodrugs, tautomers, alternate solid forms, non-covalent complexes, and combinations thereof, of a chemical entity of a depicted structure or chemical name.

A pharmaceutically acceptable salt is any salt of the parent compound that is suitable for administration to an animal or human. A pharmaceutically acceptable salt also refers to any salt which may form in vivo as a result of administration of an acid, another salt, or a prodrug which is converted into an acid or salt. A salt comprises one or more ionic forms of the compound, such as a conjugate acid or base, associated with one or more corresponding counter-ions. Salts can form from or incorporate one or more deprotonated acidic groups (e.g. carboxylic acids), one or more protonated basic groups (e.g. amines), or both (e.g. zwitterions).

A prodrug is a compound which is converted to a therapeutically active compound after administration. For example, conversion may occur by hydrolysis of an ester group or some other biologically labile group. Prodrug preparation is well known in the art. For example, "Prodrugs and Drug Delivery Systems," which is a chapter in Richard B. Silverman, *Organic Chemistry of Drug Design and Drug Action,* 2d Ed., Elsevier Academic Press: Amsterdam, 2004, pp. 496-557, provides further detail on the subject. In particular, alkyl esters having such as methyl, ethyl, isopropyl, and the like are contemplated. Also contemplated are prodrugs containing a polar group such as hydroxyl or morpholine. Examples of such prodrugs include compounds containing the moieties —$CO_2(CH_2)_2OH$,

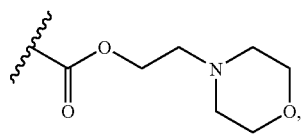

and the like.

Tautomers are isomers that are in rapid equilibrium with one another. For example, tautomers may be related by transfer of a proton, hydrogen atom, or hydride ion.

Unless stereochemistry is explicitly and unambiguously depicted, a structure is intended to include every possible stereoisomer, both pure or in any possible mixture.

Alternate solid forms are different solid forms than those that may result from practicing the procedures described herein. For example, alternate solid forms may be polymorphs, different kinds of amorphous solid forms, glasses, and the like.

Non-covalent complexes are complexes that may form between the compound and one or more additional chemical species that do not involve a covalent bonding interaction between the compound and the additional chemical species. They may or may not have a specific ratio between the compound and the additional chemical species. Examples might include solvates, hydrates, charge transfer complexes, and the like.

A dashed line represents the presence or absence of a bond. Thus, compounds according the structural formulas below are contemplated.

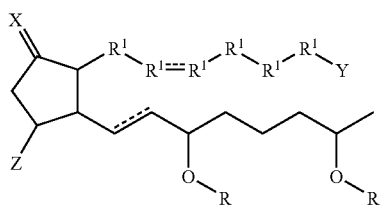

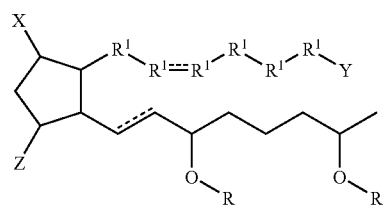

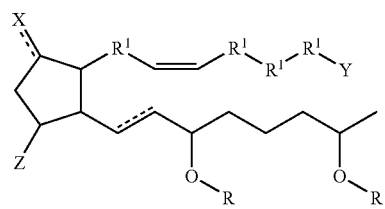

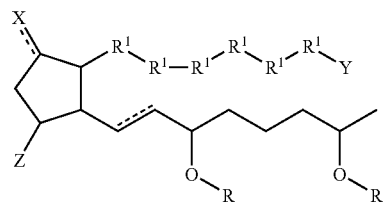

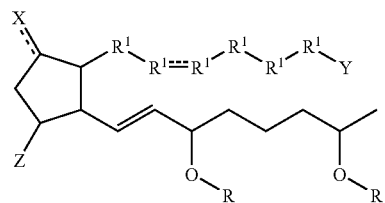

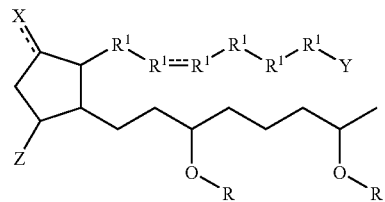

Y is an organic acid functional group, or an amide or ester thereof; or Y is hydroxymethyl or an ether thereof; or Y is a tetrazolyl functional group. For the purposes of this disclosure, Y is limited to from 0 to 14 carbon atoms, from 0 to 5 oxygen atoms, from 0 to 2 nitrogen atoms, from 0 to 2 sulfur atoms, from 0 to 1 phosphorous, and any necessary hydrogen atoms.

An organic acid functional group is an acidic functional group on an organic molecule. While not intending to be limiting, organic acid functional groups may comprise an oxide of carbon, sulfur, or phosphorous. Thus, while not intending to limit the scope of the invention in any way, in certain compounds Y is a carboxylic acid, sulfonic acid, or phosphonic acid functional group.

Esters and amides of organic acid functional groups contain have a nitrogen or an oxygen atom directly attached to the acidic core atom, where the oxygen atom is not part of an —OH moiety. The acidic core atom is the atom that is bonded to —OH or —SH in the organic acid functional group. For example, esters of amides of carboxylic acids, sulfonic acid, and phosphonic acid functional groups are depicted below.

Acids

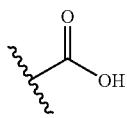 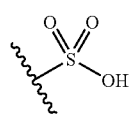 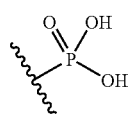

carboxylic acid     sulfonic acid     phosphonic acid

Esters

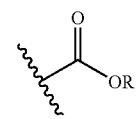 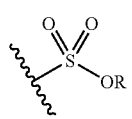 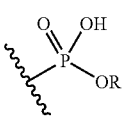

carboxylic acid ester     sulfonic acid ester     phosphonic acid ester

Amides

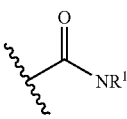 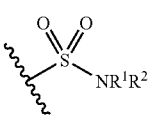 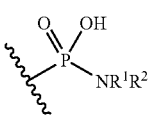

carboxylic acid amide     sulfonic acid amide     phosphonic acid amide

An amide may also have an —SO$_2$— moiety. For example the amide —CONHSO$_2$R$^3$, wherein R$^3$ is a hydrocarbyl of from 1 to 14 carbon atoms, is contemplated. R, R$^1$, R$^2$, and R$^3$ are hydrocarbyl subject to the constraint that Y may not have more than 14 carbon atoms.

Hydrocarbyl is a moiety consisting of carbon and hydrogen, including, but not limited to:
a. alkyl, which is hydrocarbyl that contains no double or triple bonds, such as:
    linear alkyl, e.g. methyl, ethyl, n-propyl, n-butyl, n-pentyl, n-hexyl, etc.,
    branched alkyl, e.g. iso-propyl, t-butyl and other branched butyl isomers, branched pentyl isomers, etc.,
    cycloalkyl, e.g. cyclopropyl, cyclobutyl, cyclopentyl, cyclohexyl, etc.,
    combinations of linear, branched, and/or cycloalkyl;
b. alkenyl, which is hydrocarbyl having 1 or more double bonds, including linear, branched, or cycloalkenyl;
c. alkynyl, which is hydrocarbyl having 1 or more triple bonds, including linear, branched, or cycloalkynyl;
d. unsubstituted or hydrocarbyl substituted phenyl; and
e. combinations of alkyl, alkenyl, and/or alkynyl C$_{1-6}$ hydrocarbyl is hydrocarbyl having 1, 2, 3, 4, 5, or 6 carbon atoms.

C$_{1-6}$ alkyl is alkyl having 1, 2, 3, 4, 5, or 6, carbon atoms such as methyl, ethyl, propyl isomers, butyl isomers, pentyl isomer, and hexyl isomers, etc.

An unsubstituted tetrazolyl functional group has two tautomeric forms, which can rapidly interconvert in aqueous or biological media, and are thus equivalent to one another. These tautomers are shown below.

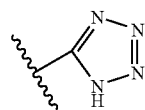 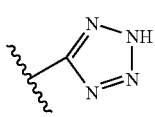

Additionally, if R$^2$ is C$_1$-C$_6$ alkyl, phenyl, or biphenyl, other isomeric forms of the tetrazolyl functional group such as the one shown below are also possible, unsubstituted and hydrocarbyl substituted tetrazolyl up to C$_{14}$ are considered to be within the scope of the term "tetrazolyl."

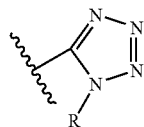

In one embodiment, Y is —CO$_2$R$^4$, —CONR$^5$R$^6$, —CON(CH$_2$CH$_2$OH)$_2$, —CONH(CH$_2$CH$_2$OH), —CH$_2$OH, —P(O)(OH)$_2$, —CONHSO$_2$R$^4$, —SO$_2$NR$^5$R$^6$,

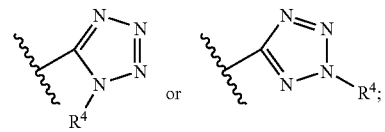

wherein R$^4$, R$^5$ and R$^6$ are independently H, C$_1$-C$_6$ alkyl, C$_{1-6}$ hydroxyalkyl, unsubstituted phenyl, or unsubstituted biphenyl, provided that Y has no more than 14 carbon atoms.

X is halo, =O, =S, —SH, —CF$_3$, —CN, =CH$_2$, =CHalkyl or =C(alkyl)$_2$ having from 1 to 6 carbon atoms. Thus, compounds according to the structural formulas below are contemplated.

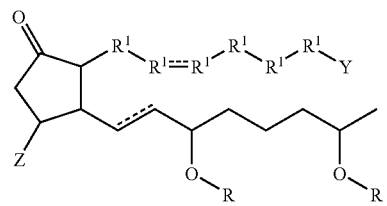

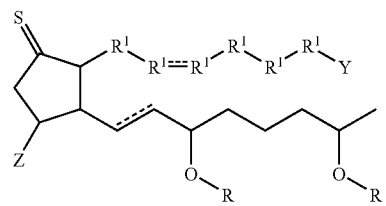

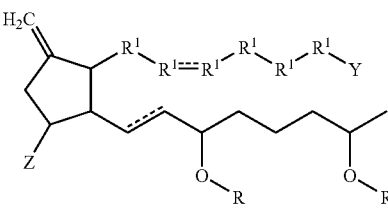

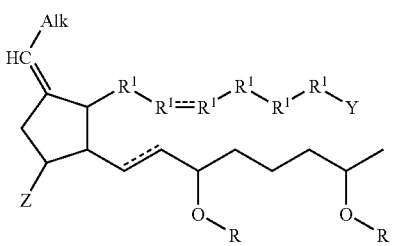

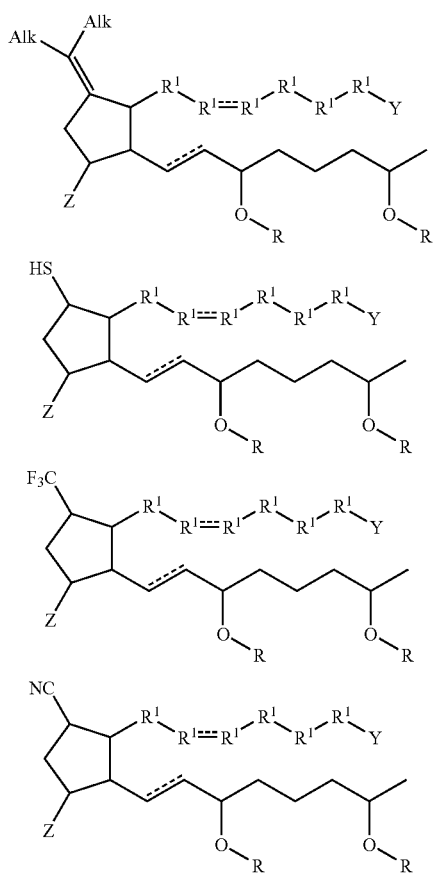
Z is halo, —OH, —OR, —SH, —CF₃, or —CN. Thus, compounds according to the structural formulas below are contemplated.
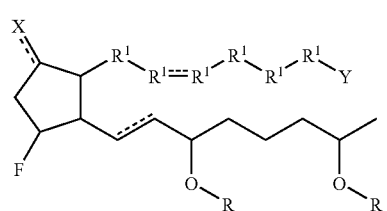
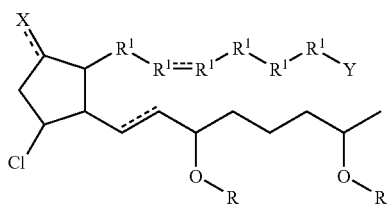
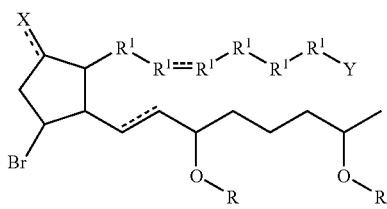
Each $R^1$ is independently O, S, $CH_2$, or if $R^1$ forms a double bond to another $R^1$, then both are CH, provided that O—O, S—O, and O—S are not present. Thus, the chain formed by the $R^1$ groups may be one of those shown below.

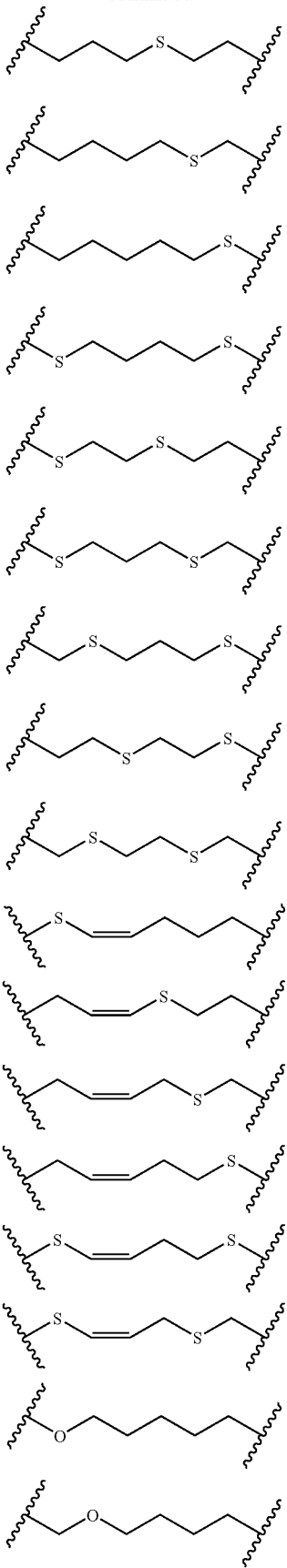
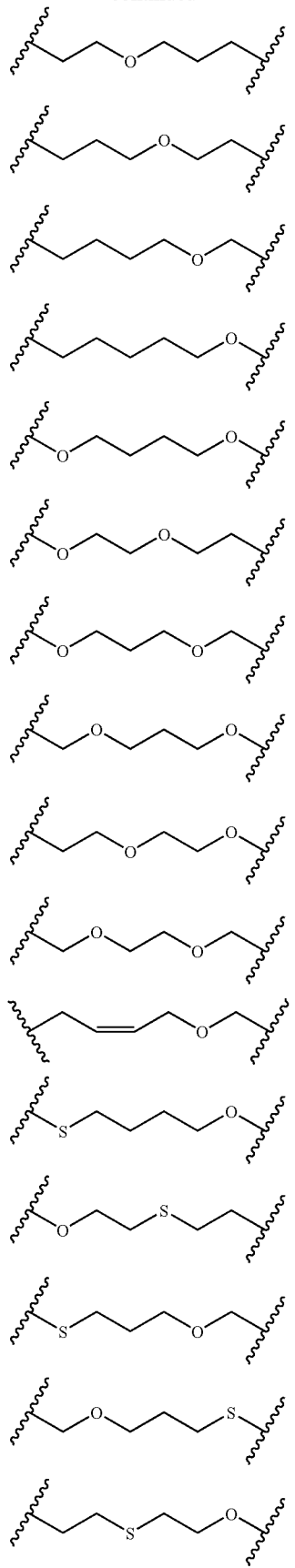

-continued

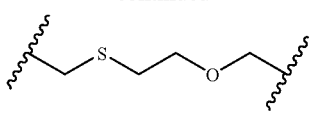

Each R is independently —H, $C_{1-6}$ alkyl, $C_{1-6}$ hydroxyalkyl, or $C_{1-6}$ acyl.

Hydroxyalkyl is alkyl having a hydroxyl attached. The hydroxyl could be attached at any position. $C_{1-6}$ hydroxyalkyl has from 1 to 6 carbon atoms.

Acyl is

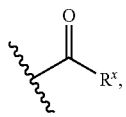

wherein Rx is hydrocarbyl. $C_{1-6}$ acyl has from 1 to 6 carbon atoms.

Structural representations of useful embodiments are depicted below.

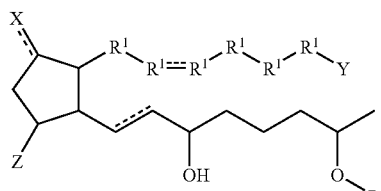
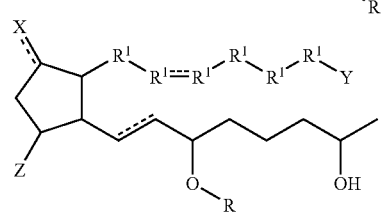
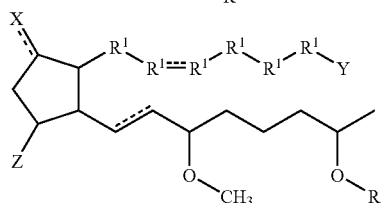
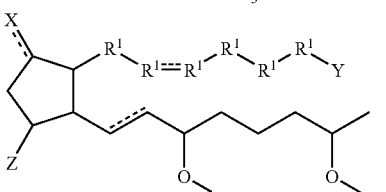
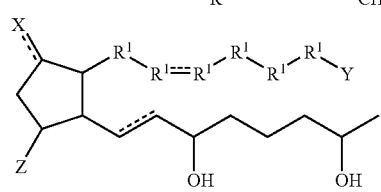

-continued

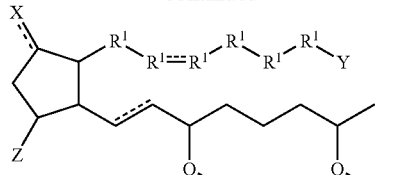
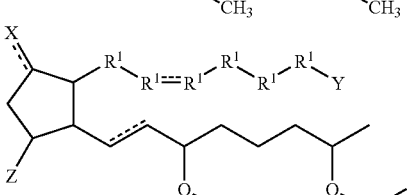
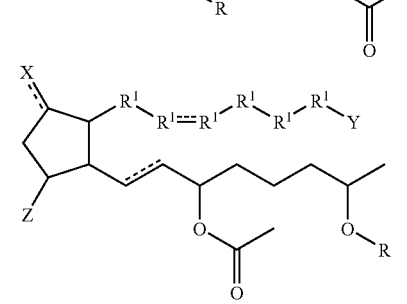
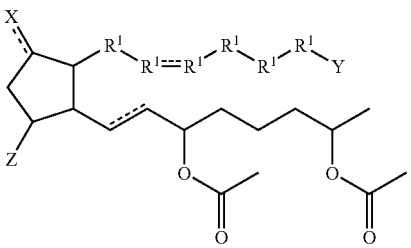

In one embodiment, X is Cl.
In another embodiment, Z is OH.
In another embodiment, Z is OH.
Another embodiment is a compound represented by the formula

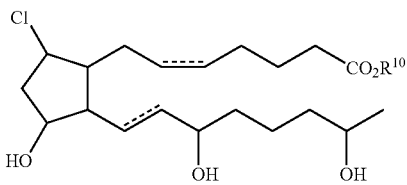

wherein $R^{10}$ is H or $C_{1-6}$ alkyl.

Another embodiment is a compound represented by the formula

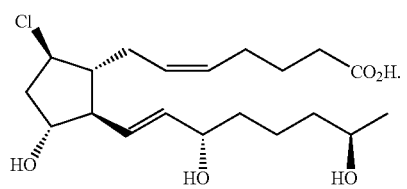 [SMILES: C[C@@H](O)CCC[C@H](O)/C=C/[C@@H]1[C@@H](C/C=C\CCCC(=O)O)[C@H](Cl)C[C@H]1O]

Another embodiment is a compound represented by the formula

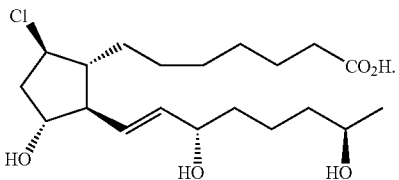 [SMILES: C[C@@H](O)CCC[C@H](O)/C=C/[C@@H]1[C@@H](CCCCCCC(=O)O)[C@H](Cl)C[C@H]1O]

Another embodiment is a compound represented by the formula

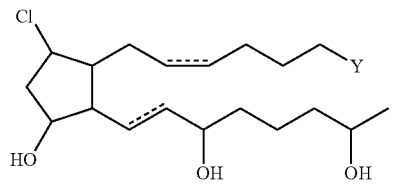

wherein a dashed line represents the presence or absence of a bond, and

Y is $CO_2(CH_2)_2OH$ or

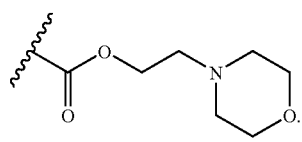 [SMILES: *C(=O)OCCN1CCOCC1]

Another embodiment is method of reducing intraocular pressure comprising administering a compound disclosed herein to a mammal in need thereof.

Another embodiment is a method of treating glaucoma or ocular hypertension comprising administering a compound disclosed herein to a mammal in need thereof.

Another embodiment is a method of growing hair or improving the appearance of hair comprising administering a compound disclosed herein to a mammal in need thereof.

Another embodiment is use of a compound disclosed herein in the manufacture of a medicament for the treatment of glaucoma or ocular hypertension.

Another embodiment is use of a compound disclosed herein in the manufacture of a medicament for growing hair or improving the appearance of hair.

Other hypothetical examples of useful compounds are depicted below.

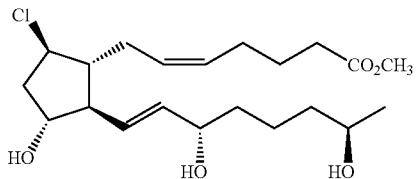

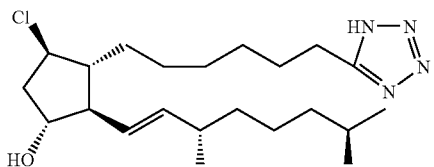

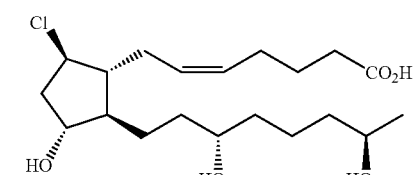

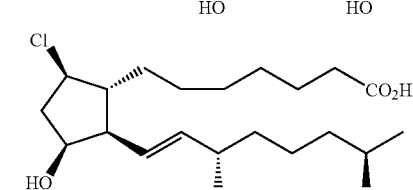

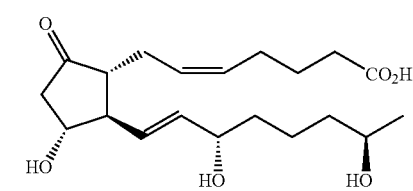

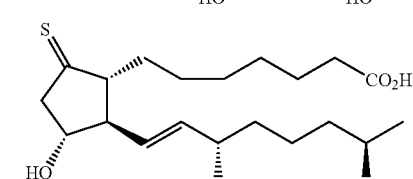

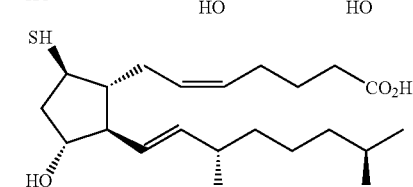

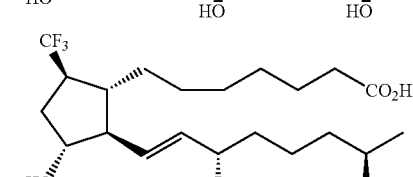

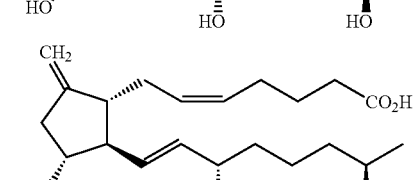

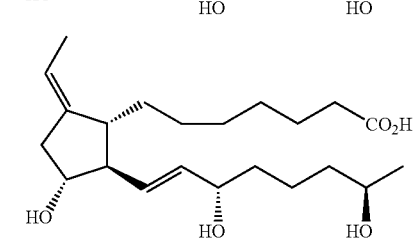

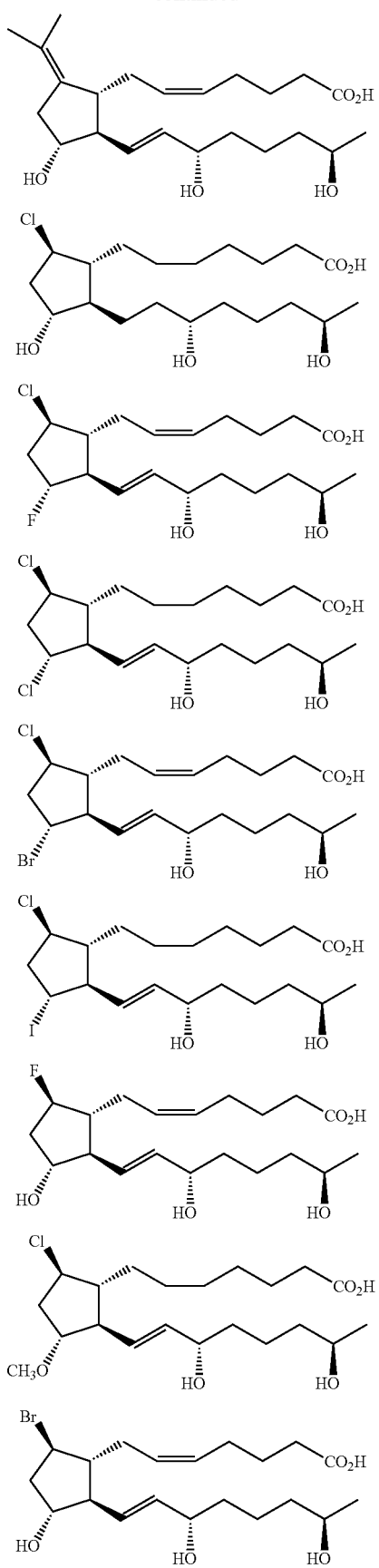
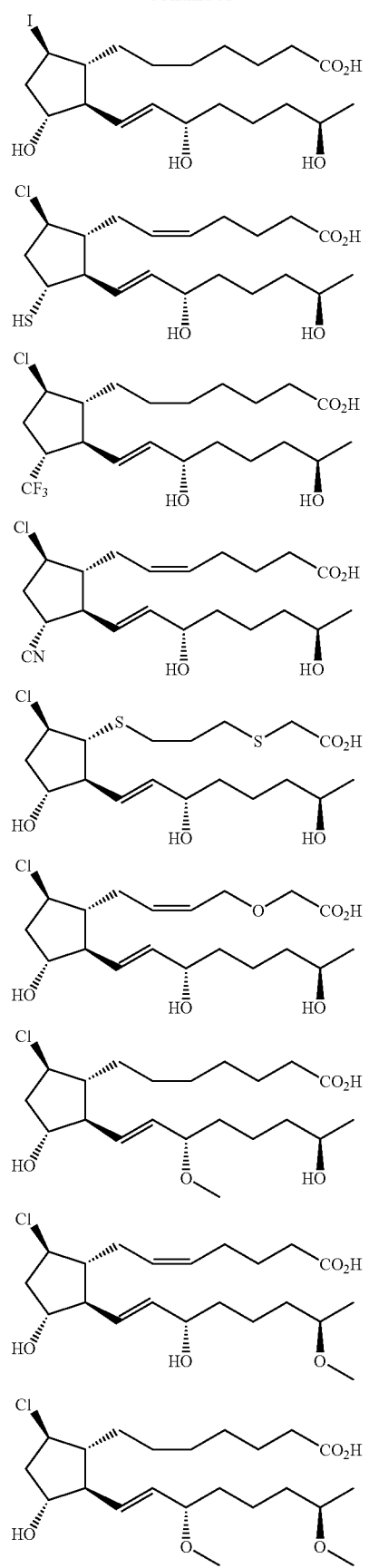

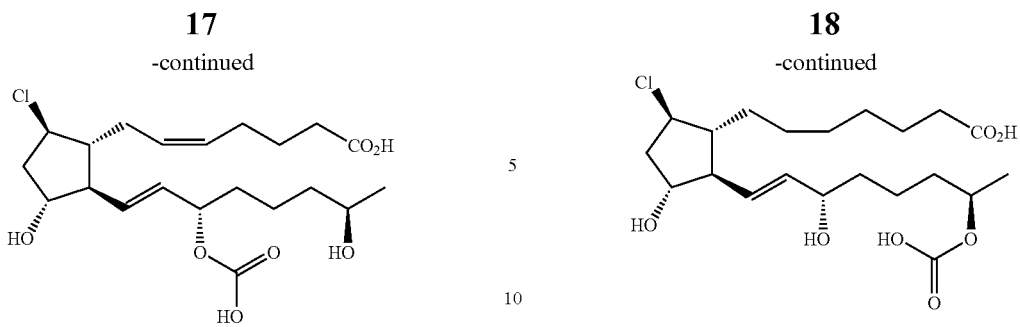
Synthetic Methods
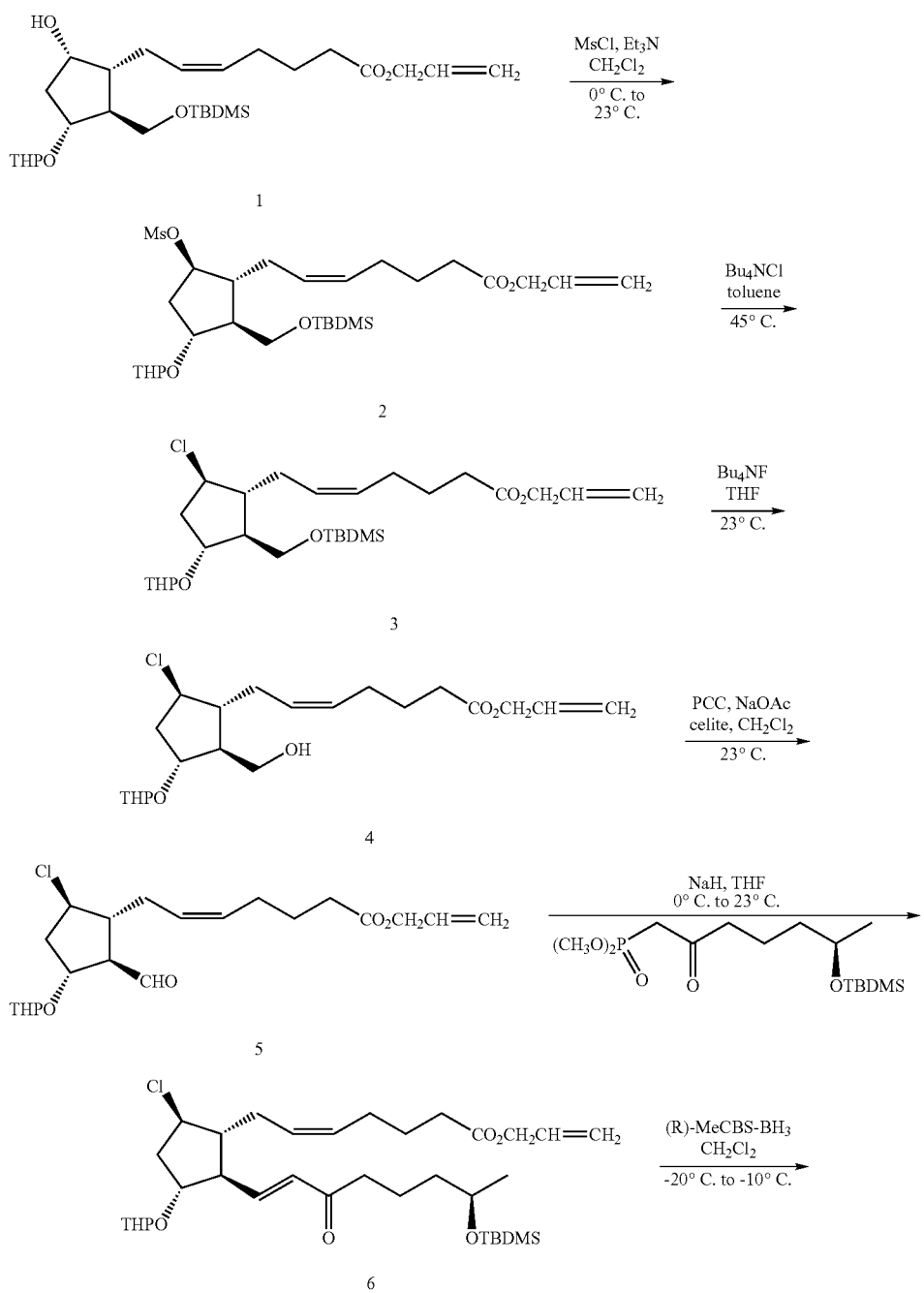

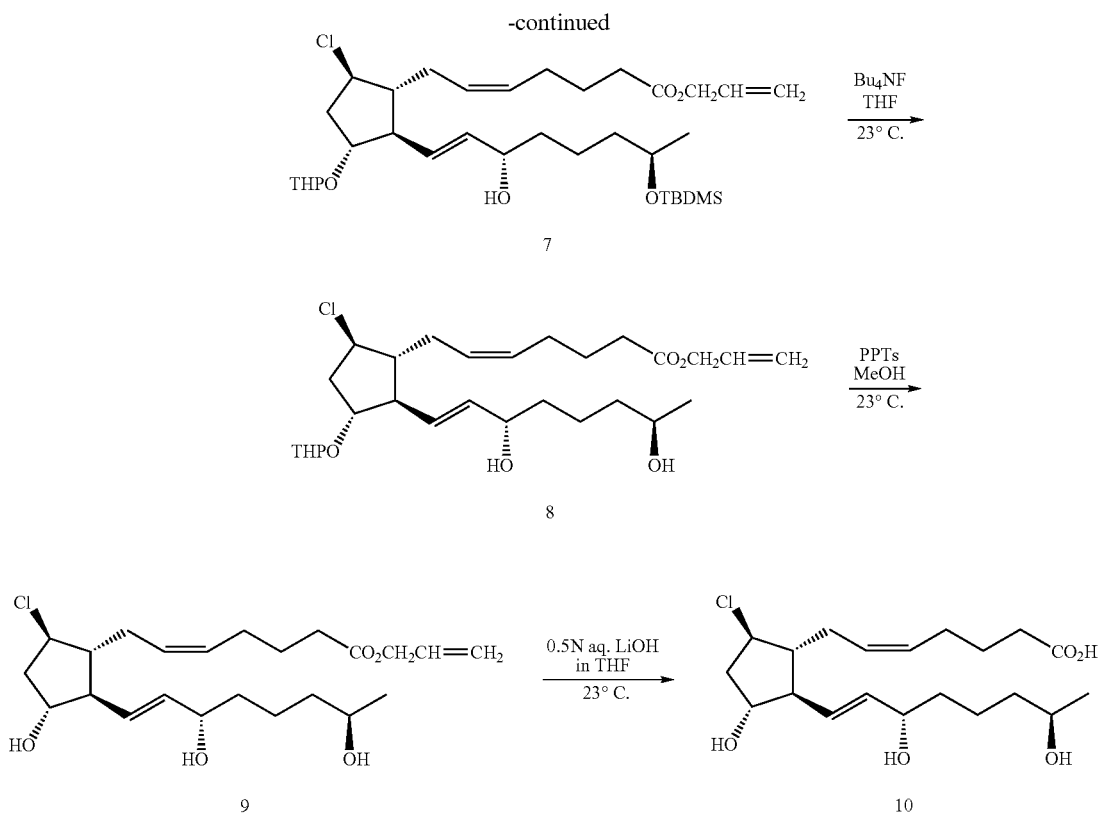

(Z)-allyl 7-((1R,2S,3R,5S)-2-((tert-butyldimethylsilyloxy)methyl)-5-(methylsulfonyloxy)-3-(tetrahydro-2H-pyran-2-yloxy)cyclopentyl)hept-5-enoate (2)

To a solution of silyl ether 1 (5 g, 10 mmol) and triethylamine (5 g, 49.5 mmol) in 40 mL of dichloromethane at 0° C. was added dropwise with rapid stirring, 2 mL (25.8 mmol) of mesyl chloride. After completion of addition the ice bath was removed and the reaction mixture was stirred at room temperature over 1 h. TLC analysis showed no starting material left (Rf=0.5 in 20% EtOAc-hexanes). The mixture was filtered through 50 g of silica gel and washed with 250 mL of 1:1 hexanes:EtOAc. The filtrate was concentrated in vacuo to yield 6.2 g (107% yield) of crude mesylate 2 containing some solvent and triethylamine hydrochloride. $^1$H NMR (CDCl$_3$): 0.04 (s, 6H), 0.87 (s, 9H), 1.25 (m, 1H), 1.44-1.84 (m, 9H), 1.85-2.38 (m, 10H), 2.99 (s, 1.3H), 3.03 (s, 1.3H), 3.14 (s, 1.7H), 3.48 (m, 1H), 3.68 (m, 2H), 3.85 (m, 1.5H), 4.10 (m, 0.6H), 4.20 (m, 0.6H), 4.58 (m, 3H), 5.06 (m, 1H), 5.26 (m, 2H), 5.42 (m, 2H), 5.91 (m, 1H).

(Z)-allyl 7-((1R,2S,3R,5R)-2-((tert-butyldimethylsilyloxy)methyl)-5-chloro-3-(tetrahydro-2H-pyran-2-yloxy)cyclopentyl)hept-5-enoate (3)

A solution of 10 mmol of mesylate 2 and 11.15 g (40 mmol) of tetra-n-butylammonium chloride in 200 ml of toluene was stirred at 45° C. for 20 h, then 23° C. for 40 h. The reaction mixture was then diluted with ethyl acetate (250 mL) and transferred into a 1 L size separatory funnel. The organic layer was washed with water (2×500 μL), brine (200 mL), dried over anhydrous sodium sulfate (100 g), and filtered. Concentration of the filtrate in vacuo gave 4.7 g of crude products. Flash column chromatographic purification (FCC) of the crude mixture on a 120 g size silica gel cartridge eluted with 5% EtOAc-95% hexanes (1.5 L), 10% EtOAc-90% hexanes (500 mL), then straight ethyl acetate yielded 1.48 g (29%) of chloride 3; $^1$H NMR (CDCl$_3$): 0.04 (s, 6H), 0.89 (s, 9H), 3.4-3.77 (m, 3H), 3.78-4.2 (m, 3H), 4.3-4.7 (m, 3H), 5.2-5.58 (m, 4H), 5.93 (m, 1H). Also obtained was 2.2 g of a more polar by-product. This by-product was further purified by FCC on 120 g of silica gel eluted with 20% EtOAc-80% hexanes then 1L 40% EtOAc-hexanes to yield 690 mg of desilylated chloride 3; $^1$H NMR (CDCl$_3$): 1.42-1.98 (m, 12H), 2.0-2.48 (m, 8H), 3.45-4.44 (m, 6H), 4.54-4.76 (m, 3H), 5.20-5.55 (m, 4H), 5.91 (m, 1H).

(Z)-allyl 7-((1R,2S,3R,5R)-5-chloro-2-(hydroxymethyl)-3-(tetrahydro-2H-pyran-2-yloxy)cyclopentyl)hept-5-enoate (4)

A solution of 1.46 g (2.8 mmol) of silyl ether 3 in 10 mL of 1.0M TBAF/THF was stirred at 25° C. for 3 h. The THF solvent was then removed in vacuo and the residual oil was taken up in ethyl acetate (100 mL) and washed with 2×75 mL of saturated aqueous ammonium chloride, brine, and dried over anhydrous sodium sulfate (50 g). The mixture was then filtered and the filtrate was concentrated in vacuo to yield 1.18 g (quantitative yield) of alcohol 4 used in the next step without purification; $^1$H NMR (CDCl$_3$): 1.42-1.98 (m, 12H), 2.0-2.48 (m, 8H), 3.45-4.44 (m, 6H), 4.54-4.76 (m, 3H), 5.20-5.55 (m, 4H), 5.91 (m, 1H).

(Z)-allyl 7-((1R,2R,3R,5R)-5-chloro-2-formyl-3-(tetrahydro-2H-pyran-2-yloxy)cyclopentyl)hept-5-enoate (5)

A solution of 690 mg (1.72 mmol) of alcohol 4 in 4 mL of dichloromethane was added via pipette to a mixture of PCC (650 mg, 3.0 mmol), sodium acetate (325 mg, 3.96 mmol), and Celite (1.23 g) in 7 mL of DCM. The pipette was rinsed with an additional 3 mL of DCM to complete the transfer. The mixture was stirred sealed at 25° C. for 3 h. The mixture was worked up by filtration through 25 g of silica gel and washed with 200 mL of 1:4 EA:hexanes. The filtrate was concentrated in vacuo to yield 500 mg (72% yield) of crude aldehyde 5 as an oil; $^1$H NMR (CDCl$_3$): 1.45-1.85 (m, 10H), 2.04-3.00 (m, 10H), 3.51 (m, 1H), 3.81 (m, 1H), 4.07 (m, 1H), 4.59 (m, 4H), 5.26 (m, 1H), 5.45 (m, 1H), 5.92 (m, 1H), 9.75 (dd, J=2.1, 9 Hz, 1H).

(Z)-allyl 7-((1R,2R,3R,5R)-2-((R,E)-8-(tert-butyldimethylsilyloxy)-7-methyl-3-oxooct-1-enyl)-5-chloro-3-(tetrahydro-2H-pyran-2-yloxy)cyclopentyl)hept-5-enoate (6)

To a suspension of 56 mg (1.35 mmol) of sodium hydride (60% oil dispersion) in 1 ml of THF at 0° C. was added a solution of dimethyl (6R)-6-{[tert-butyl(dimethyl)silyl]oxy}-2-oxoheptylphosphonate (550 mg, 1.57 mmol) in 1 mL THF. The mixture was stirred at 0° C. for 30 min before a solution of aldehyde 5 (500 mg, 1.25 mmol) in 1 ml of THF was added dropwise. The syringe containing the aldehyde 5 was rinsed with 2 mL of THF to complete the addition and the mixture was stirred at 25° C. for 3 h. The reaction was worked up with addition of saturated aqueous ammonium chloride (50 mL) and the aqueous layer was extracted with ethyl acetate (2×75 mL). The ethyl acetate layers were combined and washed with brine, dried over 30 g of anhydrous sodium sulfate, filtered and concentrated in vacuo to yield 920 mg of crude products. Flash chromatographic purification using a 40 g silica gel cartridge eluted with 10% EtOAc-hexanes yielded 490 mg (63%) of purified enone 6; $^1$H NMR (CDCl$_3$): 0.04 (s, 6H), 0.88 (s, 9H), 1.12 (d, J=6 Hz, 3H), 1.36-1.80 (m, 13H), 1.98-2.42 (m, 9H), 2.54 (t, J=7.2 Hz, 2H), 3.44 (m, 1H), 3.78 (m, 2H), 3.90-4.30 (m, 2H), 4.57 (m, 3H), 5.20-5.52 (m, 4H), 5.91 (m, 1H), 6.14 (m, 1H), 6.74 (m, 1H). LC-MS 625.48 [M$^+$+CH$_3$CN].

(Z)-allyl 7-((1R,2R,3R,5R)-2-((3S,7R,E)-7-(tert-butyldimethylsilyloxy)-3-hydroxyoct-1-enyl)-5-chloro-3-(tetrahydro-2H-pyran-2-yloxy)cyclopentyl)hept-5-enoate (7)

A solution of enone 6 (398 mg, 0.64 mmol) in 7 mL of dichloromethane was cooled to −20° C. and stirred rapidly while solid (R)-methylCBS-borane complex (290 mg, 1.0 mmol) was added in one portion. The resulting solution was stirred at −20° to −10° C. for 1 h. TLC analysis at this stage showed no starting material left and the reaction mixture was quenched with 2 mL of methanol, the cooling bath was removed and the mixture was stirred at 20° C. 60 min. The mixture was concentrated in vacuo to remove solvents and the residual products were purified by FCC on silica gel (40 g Silicycle cartridge) to yield 270 mg of (15S)-alcohol 7; $^1$H NMR (CDCl$_3$): 0.03 (s, 6H), 0.87 (s, 9H), 1.10 (d, J=6 Hz, 3H), 1.20-1.97 (m, 18H), 2.0-2.4 (m, 8H), 3.45 (m, 1H), 3.80 (m, 2H), 3.90-4.15 (m, 3H), 4.59 (m, 3H), 5.20-5.70 (m, 6H), 5.92 (m, 1H).

(Z)-allyl 7-((1R,2R,3R,5R)-5-chloro-2-((3S,7R,E)-3,7-dihydroxyoct-1-enyl)-3-(tetrahydro-2H-pyran-2-yloxy)cyclopentyl)hept-5-enoate (8)

A solution of silyl ether 7 (270 mg, 0.43 mmol) was stirred at 30° C. with 2 mL (2 mmol) of 1.0M TBAF/THF in a vial for 20 h. TLC indicated starting material was mostly desilylated and the reaction was concentrated in vacuo. The residual crude products were taken up in 50 mL of ethyl acetate and washed sequentially with saturated ammonium chloride (50 mL), brine (50 mL), and dried over 10 g of anhydrous sodium sulfate. The mixture was filtered and concentrated in vacuo. The residual products were purified by flash column chromatography on 20 g of silica gel eluted in 1:1 hexanes:EtOAc, then straight EtOAc. Combination of appropriate fractions and removal of the solvents yielded 175 mg (79%) of pure diol 8 as an oil; $^1$H NMR (CDCl$_3$): 1.18 (d, J=6 Hz, 3H), 1.38-1.84 (m, 13H), 1.91 (m, 1H), 2.00-2.40 (m, 11H), 3.47 (m, 1H), 3.81 (m, 2H), 3.99 (m, 1H), 4.09 (m, 2H), 4.54-4.72 (m, 3H), 5.21-5.66 (m, 6H), 5.92 (m, 1H).

(Z)-Allyl 7-((1R,2R,3R,5R)-5-chloro-2-((3S,7R,E)-3,7-dihydroxyoct-1-enyl)-3-hydroxycyclopentyl)hept-5-enoate (9)

A 20 mL vial equipped with a magnetic stirbar was charged with 175 mg (0.34 mmol) of TAP-ether 8 dissolved in 5 mL of methanol. To this was then added 300 mg (1.20 mmol) of pyridinium p-toluenesulfonate and the mixture was stirred at 22° C. over 7.5 h. The reaction was sampled by TLC (R$_f$ of product was 0.6 in EtOAc) and worked up by concentration in vacuo to remove methanol. The residual products were taken up in ethyl acetate and filtered through a 22 g plug of silica gel, eluting the polar product away from the salts with ethyl acetate (350 mL). Concentration of the filtrate yielded 125 mg of product triol 9 as an oil; $^1$H NMR (CDCl$_3$): 1.18 (d, J=6.3 hz, 3H), 1.34-1.62 (m, 5H), 1.69 (m, 2H), 1.84-2.38 (m, 11H), 2.47 (br s, 1H), 3.53 (br s, 1H), 3.70 (br s, 1H), 3.79 (br m, 1H), 3.99 (m, 1H), 4.08 (m, 2H), 4.57 (m, 2H), 5.18-5.60 (m, 6H), 5.91 (m, 1H).

(Z)-7-((1R,2R,3R,5R)-5-chloro-2-((3S,7R,E)-3,7-dihydroxyoct-1-enyl)-3-hydroxycyclopentyl)hept-5-enoic Acid (10)

A solution of 77 mg (0.18 mmol) of ester 9 in 1.4 mL of THF was hydrolyzed with 400 uL (0.18 mmol) of aqueous lithium hydroxide (0.5M) and 0.4 mL of methanol at 25° C. for 5 h. The mixture was acidified by addition of 200 uL of 1.0M hydrochloric acid and the residual water was removed in vacuo. The residual products were purified by FCC on 10 g of silica gel eluted with 100% EtOAc, 5% methanol:95% EtOAc, then 10% methanol:90% ethyl acetate. Isolated from appropriate fractions was 49 mg of free acid 10 as an oil (70% yield); $^1$H NMR (acetone-d$_6$): 1.11 (d, J=6.3 Hz, 3H), 1.45 (m, 6H), 1.67 (m, 2H), 1.91 (m, 1H), 2.09-2.37 (m, 8H), 2.86 (br s, 4H), 3.71 (m, 1H), 4.12 (m, 3H), 5.54 (m, 4H).

Scheme 2
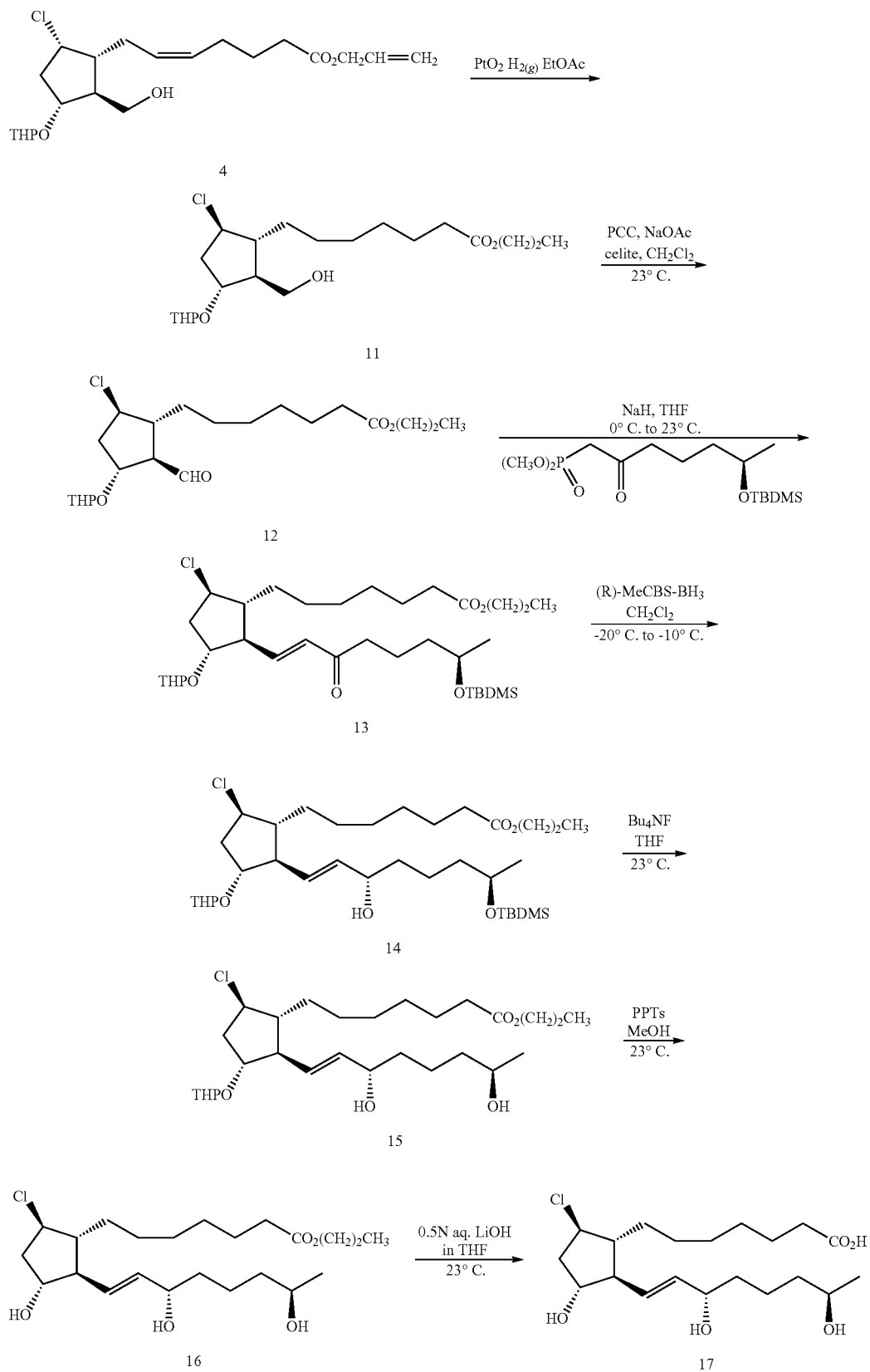

Propyl 7-((1R,2S,3R,5R)-5-chloro-2-(hydroxymethyl)-3-(tetrahydro-2H-pyran-2-yloxy)cyclopentyl) heptanoate (11)

A solution of 1 g (2.49 mmol) of alcohol 4 in 13 mL of EtOAc and Adam's catalyst (22 mg) was stirred under 30 psi of hydrogen gas in a Parr apparatus over 21 h. The mixture was then filtered to remove the catalyst through a plug of silica gel with EtOAc as solvent. The filtrate was then concentrated in vacuo yield the propyl ester 11 (990 mg) as an oil; $^1$H NMR (CDCl$_3$); 0.94 (t, J=7.3 Hz, 3H), 1.20-1.94 (m, 31H), 2.17 (m, 2H), 2.32 (m, 4H), 3.46-4.12 (m, 8H), 4.03 (t, J=6.6 Hz, 2H), 4.13-4.38 (m, 2H), 4.59 (m, 1H), 4.73 (m, 1H).

Propyl 7-((1R,2R,3R,5R)-5-chloro-2-formyl-3-(tetrahydro-2H-pyran-2-yloxy)cyclopentyl)heptanoate (12)

A solution of 700 mg (1.73 mmol) of alcohol 11 in 4 mL of dichloromethane was added via pipette to a mixture of PCC (700 mg, 3.23 mmol), sodium acetate (350 mg, 4.26 mmol), and Celite (1.3 g) in 7 mL of DCM. The pipette was rinsed with an additional 3 mL of DCM to complete the transfer. The mixture was stirred sealed at 30° C. for 1.5 h. The mixture was worked up by filtration through 20 g of silica gel and washed with 200 mL of 1:4 EA:hexanes. The filtrate was concentrated in vacuo to yield 500 mg) of crude aldehyde 12. Further FCC purification on 10 g of silica gel yielded 380 mg of purified aldehyde 12 (54% yield) as an oil; $^1$H NMR (CDCl$_3$); 0.93 (t, J=7.2 Hz, 3H), 1.31 (m, 10H), 1.42-1.90 (m, 17H), 1.94-2.44 (m, 4H), 2.28 (t, J=7.5 Hz, 2H), 2.52 (m, 1H), 2.68 (m, 1H), 3.48 (m, 2H), 3.81 (m, 2H), 4.01 (t, J=6.6 Hz, 3H), 4.06 (m, 1H), 4.5-4.64 (m, 2H), 9.75 (m, J=2.1, 9 Hz, 1H).

Propyl 7-((1R,2R,3R,5R)-2-((R,E)-7-(tert-butyldimethylsilyloxy)-3-oxooct-1-enyl)-5-chloro-3-(tetrahydro-2H-pyran-2-yloxy)cyclopentyl)heptanoate (13)

To a suspension of 56 mg (1.35 mmol) of sodium hydride (60% oil dispersion) in 1 ml of THF at 0° C. was added a solution of dimethyl (6R)-6-{[tert-butyl(dimethyl)silyl] oxy}-2-oxoheptylphosphonate (550 mg, 1.57 mmol) in 1 mL THF. The mixture was stirred at 0° C. for 30 min before a solution of aldehyde 12 (380 mg, 0.94 mmol) in 1 ml of THF was added dropwise. The syringe containing the aldehyde 12 was rinsed with 2 mL of THF to complete the addition and the mixture was stirred at 25° C. for 3 h. The reaction was worked up with addition of saturated aqueous ammonium chloride (50 mL) and the aqueous layer was extracted with ethyl acetate (2×75 mL). The ethyl acetate layers were combined and washed with brine, dried over 30 g of anhydrous sodium sulfate, filtered and concentrated in vacuo to yield 880 mg of crude products. Flash chromatographic purification using a 30 g silica gel cartridge eluted with 10% EtOAc-hexanes yielded 425 mg (71%) of purified enone 13; $^1$H NMR (CDCl$_3$): 0.04 (s, 6H), 0.88 (s, 9H), 0.93 (t, J=7.5 Hz, 3H), 1.12 (d, J=6.3 Hz, 3H), 1.22-1.84 (m, 24H), 1.97 (m, 1H), 2.19 (t, J=6.3 Hz, 1H), 2.24-2.58 (m, 6H), 3.45 (m, 1H), 3.79 (m, 2H), 4.02 (m, 3H), 4.19 (m, 1H), 4.57 (m, 1H), 6.14 (m, 1H), 6.75 (m, 1H).

Propyl 7-((1R,2R,3R,5R)-2-((3S,7R,E)-7-(tert-butyldimethylsilyloxy)-3-hydroxyoct-1-enyl)-5-chloro-3-(tetrahydro-2H-pyran-2-yloxy)cyclopentyl)heptanoate (14)

A solution of enone 13 (425 mg, 0.67 mmol) in 7 mL of dichloromethane was cooled to −30° C. and stirred rapidly while solid (R)-methylCBS-borane complex (350 mg, 1.20 mmol) was added in one portion. The resulting solution was stirred at −30° to −20° C. for 1 h. TLC analysis at this stage showed no starting material left and the reaction mixture was quenched with 2 mL of methanol, the cooling bath was removed and the mixture was stirred at 25° C. 60 min. The mixture was concentrated in vacuo to remove solvents and the residual products were purified by FCC on silica gel (40 g Silicycle cartridge, 500 mL of 10% EA-hexanes, then 500 mL of 20% EA-hexanes) to yield 316 mg (74% yield) of (15S)-alcohol 14; $^1$H NMR (CDCl$_3$): 0.04 (s, 6H), 0.87 (s, 9H), 0.93 (t, J=6 Hz, 3H), 1.10 (d, J=4.8 Hz, 3H), 1.24-1.88 (m, 24H), 2.10-2.32 (m, 4H), 3.45 (m, 1H), 3.80 (m, 2H), 4.03 (m, 4H), 4.61 (dt, J=2.4, 14.4 Hz, 1H), 5.56 (m, 2H).

Propyl 7-((1R,2R,3R,5R)-5-chloro-2-((3S,7R,E)-3,7-dihydroxyoct-1-enyl)-3-(tetrahydro-2H-pyran-2-yloxy)cyclopentyl)heptanoate (15)

A solution of silyl ether 14 (316 mg, 0.50 mmol) was stirred at 35° C. with 2 mL of 1.0M TBAF/THF in a vial for 9.5 h. TLC indicated starting material was mostly desilylated and the reaction was concentrated in vacuo. The residual crude products were taken up in 50 mL of ethyl acetate and washed sequentially with saturated ammonium chloride (50 mL), brine (50 mL), and dried over 10 g of anhydrous sodium sulfate. The mixture was filtered and concentrated in vacuo. The residual products were purified by flash column chromatography on 40 g of silica gel eluted in 1:1 hexanes:EtOAc, then straight EtOAc. Combination of appropriate fractions and removal of the solvents yielded 218 mg (84%) of diol 15 as an oil; $^1$H NMR (CDCl$_3$): 0.94 (t, J=7.5 Hz, 31H), 1.18 (d, J=6.3 Hz, 3H), 1.31 (m, 6H), 1.42-1.90 (m, 19H), 2.10-2.50 (m, 7H), 3.48 (m, 1H), 3.72-4.16 (m, 7H), 4.64 (dt, 1H), 5.57 (m, 2H).

Propyl 7-((1R,2R,3R,5R)-5-chloro-2-((3S,7R,E)-3,7-dihydroxyoct-1-enyl)-3-hydroxycyclopentyl)heptanoate (16)

A 20 mL vial equipped with a magnetic stirbar was charged with 218 mg (0.42 mmol) of THP-ether 15 dissolved in 5 mL of methanol. To this was then added 350 mg (1.39 mmol) of pyridinium p-toluenesulfonate and the mixture was stirred at 25° C. over 8 h. The reaction was sampled by TLC (R$_f$ of product was 0.5 in EtOAc) and worked up by concentration in vacuo to remove methanol. The residual products were taken up in ethyl acetate and filtered through 20 g of silica gel eluting with 300 mL of EtOAc. The filtrate was concentrated to yield 156 mg of products which were further purified by FCC through 25 g of silica gel, eluting with 1:1 EA-hexanes then 100% EA to yield 140 mg of product triol 16 as an oil; $^1$H NMR (CDCl$_3$): 0.94 (t, J=7.2 Hz, 3H), 1.17 (d, J=6 Hz, 3H), 1.22-1.72 (m, 18H), 1.91 (m, 2H), 2.05-2.36 (m, 4H), 3.30 (br s, 1H), 3.78 (m, 1H), 4.02 (m, 5H), 4.5 (m, 2H), 5.50 (m, 2H). $^{13}$C NMR: 10.53, 21.52, 22.09, 23.74, 25.03, 26.83, 29.08, 29.49, 32.90, 34.42, 36.75, 38.52, 43.59, 53.53, 57.75, 60.98, 66.06, 67.50, 72.56, 74.98, 133.27, 135.79, 174.24.

7-((1R,2R,3R,5R)-5-chloro-2-((3S,7R,E)-3,7-dihydroxyoct-1-enyl)-3-hydroxycyclopentyl)heptanoic Acid (17)

A solution of 137 mg (0.31 mmol) of ester 16 in 2 mL of THF was hydrolyzed with 800 uL (0.40 mmol) of aqueous lithium hydroxide (0.5M) and 1 mL of methanol at 25° C. for 6 h. The mixture was acidified to pH 5-6 by addition of 400 uL of 1.0M hydrochloric acid and the residual water was removed in vacuo. The residual products were purified by FCC on 10 g of silica gel eluted with 8% methanol:92% EtOAc, then 10% methanol:90% ethyl acetate. Isolated from appropriate fractions was 110 mg of free acid 17 as an oil (88% yield); $^1$H NMR (acetone-$d_6$): 1.13 (d, J=6.3 Hz, 3H), 1.16-1.68 (m, 13H), 1.86 (m, 1H), 2.0-2.24 (m, 3H), 2.29 (t, J=7.5 Hz, 2H), 3.73 (m, 1H), 4.09 (m, 3H), 5.56 (m, 2H). LC-MS 373.3 [M$^+$+1-H$_2$O].

In Vitro Testing

U.S. patent application Ser. No. 11/553,143, filed on Oct. 26, 2006, incorporated by reference herein, describes the methods used to obtain the in vitro data in Tables 1 and 2 below.

TABLE 1

| Compound | EP$_2$ | | | | | EP$_4$ | | | | EP$_1$ | EP$_3$ | DP$_2$ | TP |
| | cAMP | | Ca$^{2+}$ signal | | Binding | | Ca$^{2+}$ signal | | Binding | | | | |
| | EC$_{50}$ (nM) | % PGE$_2$ | EC$_{50}$ (nM) | % Inh | EC$_{50}$ (nM) | % PGE$_2$ | EC$_{50}$ (nM) | % Inh | EC$_{50}$ (nM) | EC$_{50}$ (nM) | EC$_{50}$ (nM) | EC$_{50}$ (nM) | EC$_{50}$ (nM) |
|---|---|---|---|---|---|---|---|---|---|---|---|---|---|
| 10 | 0.03 | 107 | 4 | 99 | 25 | 107 | 46 | 81 | 885 | 13 | 6 | 1816 | 178 |
| 17 | 1.47 | 100 | 109 | 78 | 1219 | 99 | 727 | 29 | | | | | |

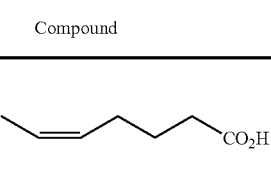

TABLE 2

| AGN-# | EP$_2$ | | | | | EP$_4$ | | | | EP$_1$ | EP$_3$ | DP$_2$ | TP |
| | cAMP | | Ca$^{2+}$ signal | | Binding | | Ca$^{2+}$ signal | | Binding | | | | |
| | EC$_{50}$ (nM) | % PGE$_2$ | EC$_{50}$ (nM) | % Inh | EC$_{50}$ (nM) | % PGE$_2$ | EC$_{50}$ (nM) | % Inh | EC$_{50}$ (nM) | EC$_{50}$ (nM) | EC$_{50}$ (nM) | EC$_{50}$ (nM) | EC$_{50}$ (nM) |
|---|---|---|---|---|---|---|---|---|---|---|---|---|---|
| 221885 low Rf | 0.2 | 97 | 9 | 95 | 338 | 106 | 154 | 42 | >10K | 41 | 26 | 4900 | 34 |

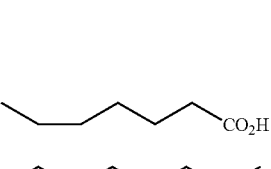

TABLE 2-continued

| AGN-# | EP2 cAMP EC50 (nM) | EP2 cAMP % PGE2 | EP2 Ca2+ signal EC50 (nM) | EP2 Ca2+ signal % Inh | EP2 Binding EC50 (nM) | EP2 Binding % PGE2 | EP4 Ca2+ signal EC50 (nM) | EP4 Ca2+ signal % Inh | EP4 Binding EC50 (nM) | EP1 EC50 (nM) | EP3 EC50 (nM) | DP2 EC50 (nM) | TP EC50 (nM) |
|---|---|---|---|---|---|---|---|---|---|---|---|---|---|
| 221886 (high Rf) | 10 | | | 52 | 8307 | | | 37 | >10K | 1231 | 633 | | 205 |
| 221909 (high Rf) | 14.5 | 87 | 413 | 67 | 3498 | 88 | 1304 | 15 | >10K | 223 | 123 | | 631 |
| 221910 (low Rf) | 0.2 | 102 | 4 | 98 | 165 | 100 | 86 | 32 | >10K | 7 | 0.3 | 910 | 71 |

What is claimed is:

1. A compound of the formula:

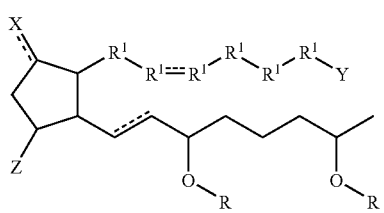

wherein a dashed line represents the presence or absence of a bond;

Y has from 0 to 14 carbon atoms and is:
an organic acid functional group, or
an amide or ester thereof;
hydroxymethyl or an ether thereof; or
a tetrazolyl functional group;

X is halo, $=$S, —SH, —$CF_3$, —CN, $=$CHalkyl or $=$C(alkyl)$_2$ having from 1 to 6 carbon atoms;

Z is halo, —OH, —OR, —SH, —$CF_3$, or —CN;

each $R^1$ is independently O, S, $CH_2$, or if $R^1$ forms a double bond to another R', then both are CH, provided that O—O, S—O, and O—S are not present, and each R is independently —H, $C_{1-6}$ alkyl, $C_{1-6}$ hydroxyalkyl, or $C_{1-6}$ acyl.

2. The compound of claim 1 wherein X is Cl or F.

3. The compound of claim 1 wherein Z is OH.

4. The compound of claim 2 wherein Z is OH.

5. The compound of claim 4 represented by the formula

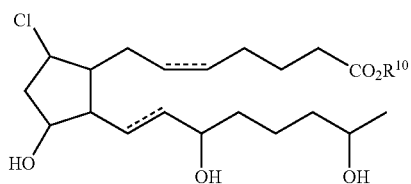

wherein $R^{10}$ is H or $C_{1-6}$ alkyl.

6. The compound of claim 5 represented by the formula

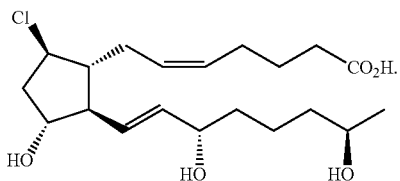

7. The compound of claim 5 represented by the formula

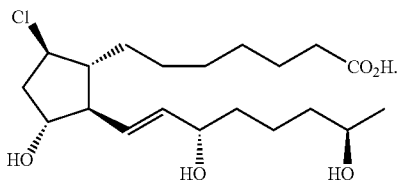 [SMILES: C[C@@H](O)CCC[C@H](O)/C=C/[C@@H]1[C@@H](CCCCCCC(=O)O)[C@H](Cl)C[C@H]1O]

8. A compound represented by the formula

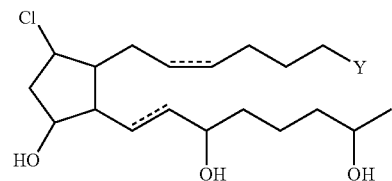

wherein a dashed line represents the presence or absence of a bond, and

Y is $CO_2(CH_2)_2OH$ or

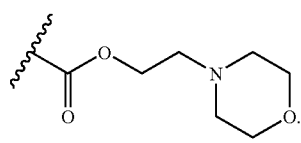 [SMILES: *C(=O)OCCN1CCOCC1]

9. A compound represented by the formula:

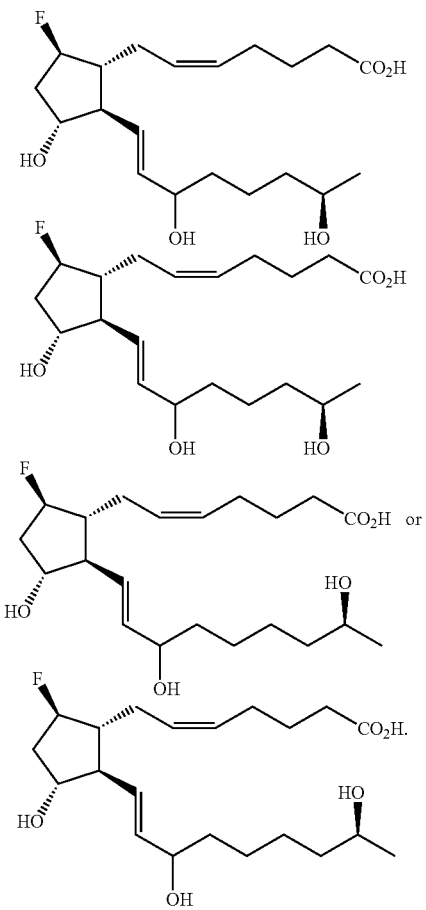

10. A method of reducing intraocular pressure comprising administering a compound according to claim 1 to a mammal in need thereof.

11. A method of treating a mammal having glaucoma or ocular hypertension comprising administering a compound according to claim 1 to said mammal.

12. A method of growing hair or improving the appearance of hair comprising administering a compound according to claim 1 to a mammal in need thereof.

\* \* \* \* \*

UNITED STATES PATENT AND TRADEMARK OFFICE
CERTIFICATE OF CORRECTION

PATENT NO. : 8,455,547 B2
APPLICATION NO. : 12/363996
DATED : June 4, 2013
INVENTOR(S) : Burk Page 1 of 1

It is certified that error appears in the above-identified patent and that said Letters Patent is hereby corrected as shown below:

In the Specification

Column 1, line 36, delete "pupilary" and insert -- pupillary --, therefor.

Column 2, line 29, delete "0-O, S-0," and insert -- O-O, S-O, --, therefor.

Column 19, line 67, delete "µL)," and insert -- mL), --, therefor.

Column 22, line 35, delete "TAP-ether" and insert -- THP-ether --, therefor.

Column 25, line 10, after "vacuo" insert -- to --.

Column 26, line 32, delete "31H)," and insert -- 3H), --, therefor.

In the Claims

Column 30, line 46, in claim 1, delete "R'," and insert -- $R^1$, --, therefor.

Signed and Sealed this
Twenty-fifth Day of March, 2014

Michelle K. Lee
*Deputy Director of the United States Patent and Trademark Office*